United States Patent
Gliner

(10) Patent No.: US 12,207,865 B2
(45) Date of Patent: *Jan. 28, 2025

(54) GUIDEWIRE WITH ABLATION AND COAGULATION FUNCTIONALITY

(71) Applicant: Biosense Webster (Israel) Ltd., Yokneam (IL)

(72) Inventor: Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 635 days.

This patent is subject to a terminal disclaimer.

(21) Appl. No.: 17/547,357

(22) Filed: Dec. 10, 2021

(65) Prior Publication Data

US 2022/0142703 A1 May 12, 2022

Related U.S. Application Data

(63) Continuation of application No. 15/293,472, filed on Oct. 14, 2016, now Pat. No. 11,213,344.

(Continued)

(51) Int. Cl.
*A61B 18/14* (2006.01)
*A61B 17/24* (2006.01)
(Continued)

(52) U.S. Cl.
CPC .......... *A61B 18/1485* (2013.01); *A61B 17/32* (2013.01); *A61B 18/1206* (2013.01);
(Continued)

(58) Field of Classification Search
CPC .......... A61B 2017/22038; A61B 2017/22042; A61B 2017/22047; A61B 2017/22048;
(Continued)

(56) References Cited

U.S. PATENT DOCUMENTS 6,033,397 A   3/2000  Laufer et al.
6,053,172 A   4/2000  Hovda et al.
(Continued)

FOREIGN PATENT DOCUMENTS

CN   1269708 A    10/2000
EP   1210021 B1   5/2006
(Continued)

OTHER PUBLICATIONS

Chinese Office Action and Search Report dated Jun. 30, 2020, for Application No. 201611032484.3, 10 pages.

(Continued)

*Primary Examiner* — Ronald Hupczey, Jr.
*Assistant Examiner* — Bradford C. Blaise
(74) *Attorney, Agent, or Firm* — FROST BROWN TODD LLP

(57) ABSTRACT

Apparatus, including a guidewire, having a distal end dimensioned to penetrate into a nasal sinus and a balloon, which is fitted over the guidewire in proximity to the distal end. There is an inflation channel, which runs along the guidewire and is coupled to convey a pressurized fluid into the balloon so as to inflate the balloon. The apparatus also includes a first electrode, fixedly attached to a distal tip of the guidewire, and a second electrode, fixedly attached to the guidewire at a location proximal to the distal tip. There are conductive leads running along the guidewire and coupled to apply an electrical potential between the first and second electrodes.

20 Claims, 4 Drawing Sheets

Related U.S. Application Data

(60) Provisional application No. 62/256,295, filed on Nov. 17, 2015.

(51) Int. Cl.

| | | |
|---|---|---|
| *A61B 17/32* | (2006.01) | |
| *A61B 18/00* | (2006.01) | |
| *A61B 18/12* | (2006.01) | |
| *A61B 34/00* | (2016.01) | |
| *A61B 34/20* | (2016.01) | |
| *A61M 25/09* | (2006.01) | |
| *A61B 17/22* | (2006.01) | |

(52) U.S. Cl.
CPC .......... *A61B 18/1492* (2013.01); *A61B 34/20* (2016.02); *A61B 34/25* (2016.02); *A61M 25/09* (2013.01); *A61B 2017/22038* (2013.01); *A61B 2017/22048* (2013.01); *A61B 17/24* (2013.01); *A61B 2017/246* (2013.01); *A61B 2017/320004* (2013.01); *A61B 2018/00077* (2013.01); *A61B 2018/0022* (2013.01); *A61B 2018/00285* (2013.01); *A61B 2018/00327* (2013.01); *A61B 2018/00577* (2013.01); *A61B 2018/00589* (2013.01); *A61B 2018/128* (2013.01); *A61B 2018/1467* (2013.01); *A61B 2034/2046* (2016.02); *A61B 2034/252* (2016.02); *A61B 2034/743* (2016.02); *A61B 2034/744* (2016.02); *A61M 2025/09008* (2013.01); *A61M 2025/09066* (2013.01)

(58) Field of Classification Search
CPC .............. A61B 2017/246; A61B 17/24; A61B 2018/00214; A61B 2018/0022; A61B 2018/00273; A61B 2018/00279; A61B 2018/00285; A61B 2018/00327; A61B 2018/00577; A61B 2018/00589; A61B 2018/128; A61B 2018/1467; A61B 18/1206; A61B 18/1485; A61B 18/1492; A61M 25/09; A61M 2025/09008; A61M 2025/09058; A61M 2025/09125; A61M 2025/09175; A61M 2025/09183
See application file for complete search history.

(56) References Cited

U.S. PATENT DOCUMENTS

| | | |
|---|---|---|
| 6,179,824 B1 | 1/2001 | Eggers et al. |
| 6,251,107 B1 * | 6/2001 | Schaer ............... A61B 18/1492 606/41 |
| 8,740,895 B2 | 6/2014 | Mayse et al. |
| 9,131,980 B2 | 9/2015 | Bloom |
| 10,772,489 B2 | 9/2020 | Govari et al. |
| 11,213,344 B2 | 1/2022 | Gliner |
| 2003/0195510 A1 * | 10/2003 | Schaer ............... A61B 18/1492 606/41 |
| 2007/0250105 A1 | 10/2007 | Ressemann et al. |
| 2009/0227900 A1 | 9/2009 | Kim et al. |
| 2010/0191151 A1 * | 7/2010 | Kwak ................ A61B 18/1492 600/585 |
| 2010/0268217 A1 | 10/2010 | Habib |
| 2012/0323227 A1 | 12/2012 | Wolf et al. |
| 2013/0253387 A1 | 9/2013 | Bonutti et al. |
| 2014/0088463 A1 | 3/2014 | Wolf et al. |
| 2014/0277072 A1 | 9/2014 | Suehara |
| 2017/0296263 A1 | 10/2017 | Zhuang et al. |

FOREIGN PATENT DOCUMENTS

| | | |
|---|---|---|
| JP | 2015-131027 A | 7/2015 |
| WO | WO 2000/050115 A2 | 8/2000 |
| WO | WO 2007/135431 A2 | 11/2007 |
| WO | WO 2008/153357 A2 | 12/2008 |

OTHER PUBLICATIONS

Chinese Office Action dated Feb. 10, 2021, for Application No. 201611032484.3, 5 pages.
European Search Report dated May 2, 2017, for Application No. 16199143.5, 8 pages.
European Communication dated Aug. 17, 2020, for Application No. 16199143.5, 5 pages.
Japanese Notification of Reasons for Refusal dated Oct. 27, 2020, for Application No. 2016-222961, 8 pages.
Japanese Final Notification of Reasons for Refusal dated Mar. 18, 2021, for Application No. 2016-222961, 2 pages.
U.S. Appl. No. 62/209,946, entitled "Automatic ENT Surgery Preplanning Using a Backtracking Maze Problem Solution," filed Aug. 26, 2015.
U.S. Appl. No. 62/221,367, entitled "Adding a Tracking Sensor to a Rigid Tool," filed Sep. 21, 2015.
U.S. Appl. No. 62/256,295, entitled "Guidewire with Ablation and Coagulation Functionality," filed Nov. 17, 2015.

* cited by examiner

GUIDEWIRE WITH ABLATION AND COAGULATION FUNCTIONALITY

CROSS-REFERENCE TO RELATED APPLICATION

This application is a continuation of U.S. patent application Ser. No. 15/293,472, entitled "Guidewire with Ablation and Coagulation Functionality," filed Oct. 14, 2016, and issued as U.S. Pat. No. 11,213,344 on Jan. 4, 2022.

U.S. patent application Ser. No. 15/293,472 claims the benefit of U.S. Provisional Patent Application 62/246,295, filed Nov. 17, 2015, which is incorporated herein by reference.

FIELD OF THE INVENTION

The present invention relates generally to surgery, and specifically to nasal sinus surgery.

BACKGROUND OF THE INVENTION

A sinuplasty procedure consists of inserting a guidewire into a desired location in the nasal sinus of a patient, and sliding a balloon to a site in the nasal sinus which is to be dilated. Once the balloon is in position, the balloon may be inflated so as to expand and dilate the region in contact with the balloon. After the dilation, the balloon may be deflated then, together with the guidewire, removed from the patient.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides apparatus, including:
a guidewire, having a distal end dimensioned to penetrate into a nasal sinus;
a balloon, which is fitted over the guidewire in proximity to the distal end;
an inflation channel, which runs along the guidewire and is coupled to convey a pressurized fluid into the balloon so as to inflate the balloon;
a first electrode, fixedly attached to a distal tip of the guidewire;
a second electrode, fixedly attached to the guidewire at a location proximal to the distal tip; and
conductive leads running along the guidewire and coupled to apply an electrical potential between the first and second electrodes.

A disclosed embodiment includes a generator, configured to generate the electrical potential as a low frequency AC (alternating current) potential, and connected to the conductive leads so as to apply the low frequency AC potential between the first and the second electrode to coagulate material proximate to the nasal sinus. Typically, the low frequency AC potential has a power of up to 5 W and a frequency of up to 30 kHz.

A further disclosed embodiment includes a generator, configured to generate the electrical potential as a high frequency AC (alternating current) potential, and connected to the conductive leads so as to apply the high frequency AC potential between the first and the second electrode to ablate material proximate to the nasal sinus. Typically, the high frequency AC potential has a power of up to 20 W and a frequency greater than 30 kHz.

In a yet further disclosed embodiment the apparatus includes an insulating section separating the distal end into a distal section comprising the distal tip, and a proximal section comprising the location proximal to the distal tip.

Another embodiment of the present invention provides apparatus, including:
a guidewire, having a distal end and a conductive section proximal to the distal end and insulated therefrom, the distal end and the section being dimensioned to penetrate into a nasal sinus;
a balloon, which is fitted over the guidewire in proximity to the distal end;
an inflation channel, which runs along the guidewire and is coupled to convey a pressurized fluid into the balloon so as to inflate the balloon;
an electrode, fixedly attached to a distal tip of the guidewire; and
conductive leads running along the guidewire and coupled to apply an electrical potential between the electrode and the proximal conductive section of the guidewire.

Another embodiment provides a method, including:
providing a guidewire, having a distal end dimensioned to penetrate into a nasal sinus;
fitting a balloon over the guidewire in proximity to the distal end;
running an inflation channel, that is coupled to convey a pressurized fluid into the balloon so as to inflate the balloon, along the guidewire;
fixedly attaching a first electrode to a distal tip of the guidewire;
fixedly attaching a second electrode to the guidewire at a location proximal to the distal tip; and
running conductive leads, that are coupled to apply an electrical potential between the first and second electrodes, along the guidewire.

Another embodiment of the present invention provides a method, including:
providing a guidewire, having a distal end and a conductive section proximal to the distal end and insulated therefrom, the distal end and the section being dimensioned to penetrate into a nasal sinus;
fitting a balloon over the guidewire in proximity to the distal end;
running an inflation channel, coupled to convey a pressurized fluid into the balloon so as to inflate the balloon, along the guidewire;
fixedly attached an electrode to a distal tip of the guidewire; and
running conductive leads, coupled to apply an electrical potential between the electrode and the proximal conductive section of the guidewire, along the guidewire.

The present disclosure will be more fully understood from the following detailed description of the embodiments thereof, taken together with the drawings, in which:

DETAILED DESCRIPTION OF EMBODIMENTS

Overview

Although a sinuplasty procedure typically involves no cutting or removal of tissue, there are cases where cutting or removal is required, for example to obtain adequate access to a particular part of a sinus. Typically, such cutting or removal is performed by a separate debrider, and/or by a tissue ablator.

Rather than requiring two separate instruments, embodiments of the present invention combine the functional aspects of an ablator and a sinuplasty guidewire into a single guidewire. A guidewire which is configured to accept a balloon for sinuplasty has two electrodes fixedly attached to the distal end of the guidewire. Passing an appropriate high frequency alternating current between the electrodes ablates tissue through which the current passes.

Alternatively or additionally, a low frequency alternating current may be passed between the electrodes. The low frequency current causes material in contact with, or in close proximity to, the electrodes to coagulate. Particularly in the case where tissue has been removed, typically generating a flow of a blood/mucus/particulate mixture, coagulation of such a mixture enhances the efficacy of the procedure.

One embodiment provides a guidewire having a distal end dimensioned to penetrate into a nasal sinus. A balloon is fitted over the guidewire in proximity to the distal end, and an inflation channel runs along the guidewire and is coupled to convey a pressurized fluid into the balloon so as to inflate the balloon. A first electrode is fixedly attached to a distal tip of the guidewire, and a second electrode is fixedly attached to the guidewire at a location proximal to the distal tip. Conductive leads run along the guidewire and are coupled to apply an electrical potential between the first and second electrodes.

An alternative embodiment provides a guidewire having a distal end and a conductive section, proximal to the distal end and insulated from the distal end. The distal end and the section are dimensioned to penetrate into a nasal sinus. A balloon is fitted over the guidewire in proximity to the distal end, and an inflation channel runs along the guidewire and is coupled to convey a pressurized fluid into the balloon so as to inflate the balloon. An electrode is fixedly attached to a distal tip of the guidewire, and conductive leads run along the guidewire and are coupled to apply an electrical potential between the electrode and the proximal conductive section of the guidewire.

Thus, embodiments of the present invention provide a single guidewire which has three functionalities: delivery of a sinuplasty balloon, ablation of tissue in proximity to the distal end of the guidewire, as well as coagulation of fluid material in proximity to the distal end.

DETAILED DESCRIPTION

Figure 1:
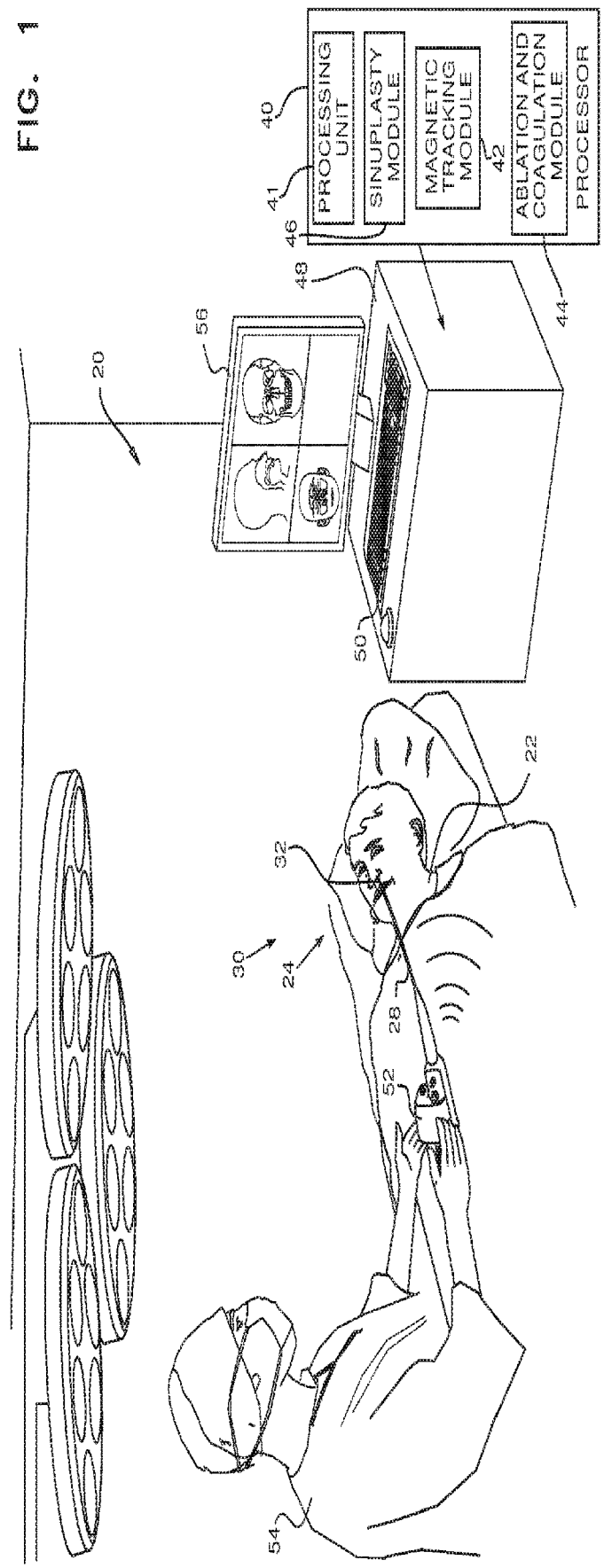
FIG. 1 is a schematic illustration of a nasal sinus surgery system, according to an embodiment of the present invention.

Reference is now made to FIG. 1, which is a schematic illustration of a nasal sinus surgery system 20, according to an embodiment of the present invention. System 20 is typically used during an invasive procedure comprising sinuplasty on a nasal sinus of a patient 22, and the system includes a guidewire 28 that is used in the sinuplasty procedure, as described in more detail below.

For the actual procedure, a set of magnetic field generators 24 are placed in proximity to the head of the patient. As is described in more detail below, guidewire 28 comprises a magnetic field sensor 30 at its distal end 32, and the field from generators 24 enables the location and orientation of the sensor, and thus of the guidewire distal end, to be tracked, after the distal end has been inserted into the nasal sinus of the patient. A system using magnetic field generators, such as generators 24, for tracking a sensor inserted into a patient is described in U.S. patent application Ser. No. 14/792,823, issued as U.S. Pat. No. 10,772,489 on Sep. 15, 2020, to Govari et al., in U.S. Provisional Patent Application 62/209,946, to Gliner, and in U.S. Provisional Patent Application 62/221,367, also to Gliner, which are incorporated herein by reference. In addition, the Carto® system produced by Biosense Webster, of Diamond Bar, CA, uses a tracking system similar to that described herein for finding the location and orientation of a coil in a region irradiated by magnetic fields.

Elements of system 20 may be controlled by a system processor 40, comprising a processing unit (PU) 41 communicating with one or more modules such as a magnetic tracking module 42, which enables the processing unit to control generators 24 and to track sensor 30. The processing unit may also communicate with an ablation and coagulation module 44 and a sinuplasty module 46, the functions of which are described below.

Processor 40 may be mounted in a console 48, which comprises operating controls 50 that typically include a keypad and/or a pointing device such as a mouse or trackball. Console 48 also connects to other elements of system 20, such as a proximal end 52 of guidewire 28. A physician 54 uses the operating controls to interact with the processor while performing the procedure, and the processor may present results produced by system 20 on a screen 56.

Processor 40 uses software stored in a memory of the processor to operate system 20. The software may be downloaded to processor 40 in electronic form, over a network, for example, or it may, alternatively or additionally, be provided and/or stored on non-transitory tangible media, such as magnetic, optical, or electronic memory.

Figure 2:
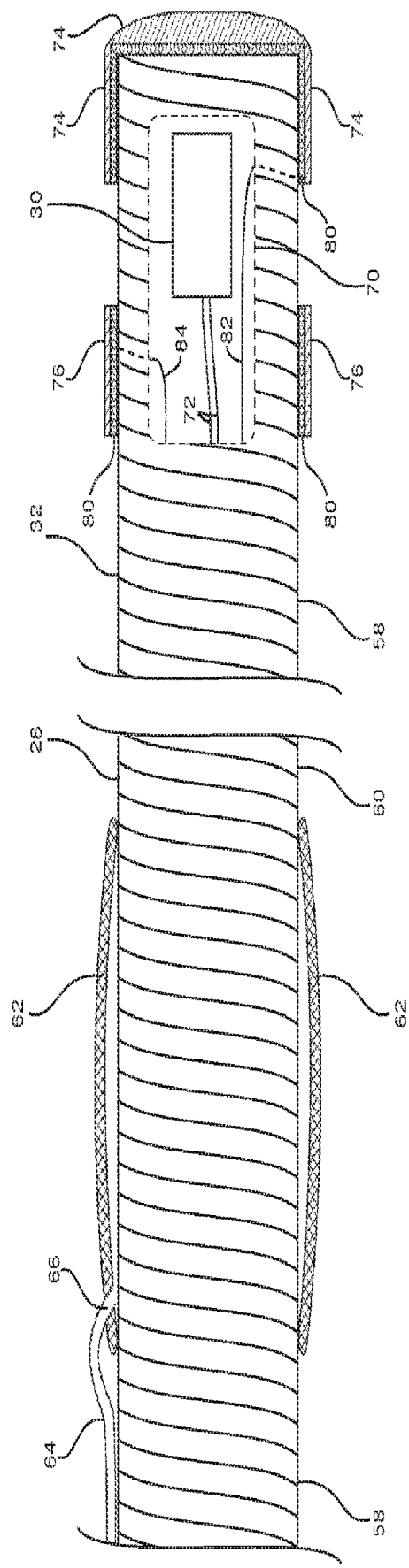
FIG. 2 is a schematic illustration of portions of a guidewire used in the system, according to an embodiment of the present invention.

FIG. 2 is a schematic illustration of portions of guidewire 28, according to an embodiment of the present invention. Guidewire 28 is typically formed as a coil 58 of stainless steel wire, and in one embodiment has an outside diameter of 0.9 mm. However, the guidewire of other embodiments of the present invention may have outer diameters that are greater than or less than 0.9 mm. FIG. 2 illustrates distal end 32 of guidewire 28, and a section 60 between the distal end and proximal end 52 (FIG. 1) of the guidewire.

As stated above, guidewire 28 is used for a sinuplasty procedure, and is configured to accept a balloon 62 that is fitted over the guidewire and that is then slid to section 60 during the procedure. The procedure typically involves pre-positioning the guidewire so that section 60 is in a desired location of a nasal sinus. Once in the desired location, processor 40 uses sinuplasty module 46 to convey a pressurized fluid, typically saline solution, via an inflation channel 64 that connects to an aperture 66 of balloon 62, so as to inflate the balloon and thus perform the sinuplasty procedure. Once the procedure has terminated, processor 40 also uses sinuplasty module 46 to remove the fluid so as to deflate the balloon, whereupon the balloon with the guidewire may be removed from the nasal sinus.

A cutaway section 70 of distal end 32 shows internal elements of the distal end. Field sensor 30 is fixedly attached to the interior of the distal end. The field sensor is typically a single axis coil having an axis of symmetry parallel to, and typically coincident with, the axis of symmetry of coil 58. Conductive wires 72 transfer signals, generated by the sensor in response to the magnetic fields from generators 24 passing through the sensor, to processor 40. Alternatively, the signals may be transferred wirelessly to processor 40. From the acquired signals, the processor is able to calculate the orientation and location of sensor 30, and thus of distal end 32.

Mounted on and external to coil 58, at the guidewire's distal end, are two electrodes—a first electrode 74, which is mounted at the distal tip of the guidewire, and a second electrode 76, which is located at the distal end proximal to the first electrode. Both electrodes are insulated by insulating material 80 from coil 58. First electrode 74 is typically in the form of a cup, and second electrode 76 is typically in the form of a ring. A conductive lead 82 conveys signals between the first electrode and processor 40, and a conductive lead 84 conveys signals between the second electrode and the processor.

During the sinuplasty procedure referred to above, guidewire 28 of system 20 performs multiple functions. Once the guidewire has been inserted to a desired position and orientation in the patient's nasal sinus, as determined by processor 40 using the signals from sensor 30, balloon 62 may be slid along the guidewire, as is described above. The balloon may be inflated to perform the sinuplasty procedure, and then deflated and removed once the procedure has concluded, as is also described above.

Simultaneously with performance of the sinuplasty procedure, or before or after the procedure, performance of other actions pertinent to the procedure may be desirable. For example, a debrider may be used to remove tissue in the region of the procedure, the debrider typically generating particulate matter within a blood/mucus mixture. Alternatively or additionally, tissue may be removed by ablation, also generating a particulate/blood/mucus mixture. It may be advantageous to coagulate the mixture produced, so as to remove it from the region of the procedure.

As described below, the first and second electrodes may be energized to provide both coagulation and ablation. A low frequency AC potential between the electrodes may be generated by processor 40, using ablation and coagulation module 44. Typically the low frequency AC is at audio frequencies, up to about 30 kHz with a power level of up to approximately 5 W and such an AC potential is known to be able to coagulate fluid such as blood or blood/particle/mucus mixtures. At least some of the coagulated material typically attaches itself to the electrodes. Alternatively or additionally, processor 40 and module 44 may be implemented to generate a high frequency AC potential between the two electrodes. Application of the high frequency AC potential serves to ablate tissue in contact with, or in close proximity to, the electrodes. The AC frequency used for ablation is usually significantly higher than the frequency used for coagulation. Typically the AC potential has a frequency of approximately 150 kHz, and a power of up to approximately 20 W, but both the frequency and the power may be varied according to the ablation desired.

Figure 3:
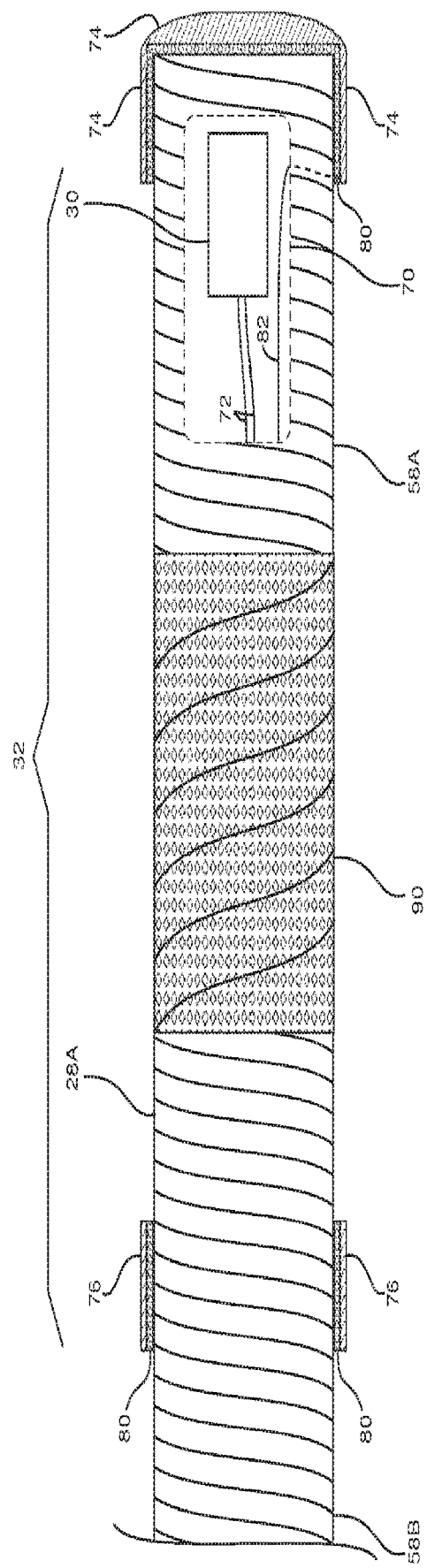
FIG. 3 is a schematic illustration of portions of an alternative guidewire used in the system, according to an embodiment of the present invention.

FIG. 3 is a schematic illustration of portions of a guidewire 28A, according to an alternative embodiment of the present invention. Apart from the differences described below, the operation of guidewire 28A is generally similar to that of guidewire 28 (FIG. 2), and elements indicated by the same reference numerals in both guidewires 28 and 28A are generally similar in construction and in operation.

For simplicity, section 60, whereon balloon 62 is slid, is not shown in FIG. 3. Rather, the figure just shows distal end 32. In contrast to guidewire 28, coil 58 of guidewire 28A is divided into two sections, a distal coil section 58A and a proximal coil section 58B. The two sections are separated by an insulating tubular section 90, typically formed from a biocompatible plastic. In some embodiments the insulating tubular section is fluted so as to be sufficiently flexible to bypass certain anatomical structures. As illustrated in the figure first electrode 74 is mounted at the distal tip of distal coil section 58A, and conductive lead 82 conveys signals between the first electrode and processor 40. Second electrode 76 overlays distal coil section 58B, and conductive lead 84 (FIG. 2) conveys signals between the second electrode and processor 40.

Figure 4:
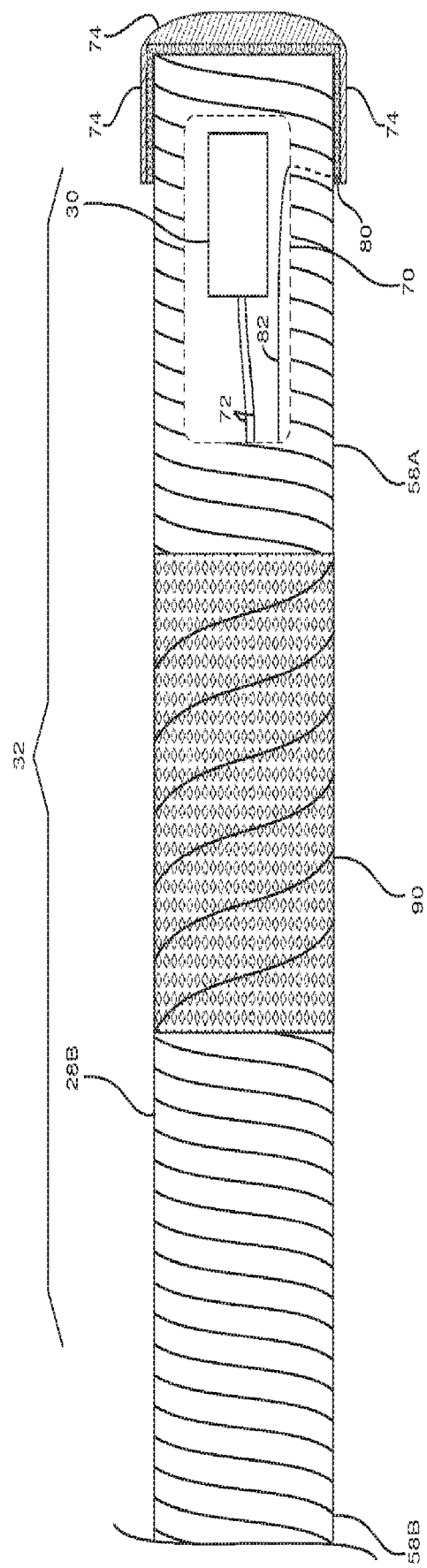
FIG. 4 is a schematic illustration of portions of a further alternative guidewire used in the system, according to an embodiment of the present invention.

FIG. 4 is a schematic illustration of portions of a guidewire 28B, according to a further alternative embodiment of the present invention. Apart from the differences described below, the operation of guidewire 28B is generally similar to that of guidewire 28A (FIG. 3), and elements indicated by the same reference numerals in both guidewires 28B and 28A are generally similar in construction and in operation.

In contrast to guidewire 28A, in guidewire 28B there is no second electrode 76 overlaying proximal coil section 58B. Rather, in guidewire 28B, proximal coil section 58B is used as a second electrode.

It will be understood that the multiple functions that guidewires 28, 28A, and 28B are able to perform, comprising sinuplasty, ablation, and coagulation, significantly enhance the efficiency of operation of the guidewires compared to prior art guidewires.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An apparatus, comprising:
   (a) a guidewire, having a distal end dimensioned to penetrate into a nasal sinus;
   (b) a balloon, which is slidably fitted directly over the guidewire in proximity to the distal end such that the balloon is in contact with the guidewire;
   (c) an inflation channel, which runs along the guidewire and is coupled to convey a pressurized fluid into the balloon so as to inflate the balloon;
   (d) a first electrode, fixedly attached to a distal tip of the guidewire;
   (e) a second electrode, fixedly attached to the guidewire at a location proximal to the distal tip, wherein the first and second electrodes are distal and separate from the balloon; and
   (f) conductive leads running along the guidewire and coupled to apply an electrical potential between the first and second electrodes so as to treat material proximate to the nasal sinus.

2. The apparatus according to claim 1, further comprising a generator, wherein the generator is configured to generate the electrical potential as a low frequency AC (alternating current) potential, and wherein the generator is connected to the conductive leads so as to apply the low frequency AC potential between the first electrode and the second electrode to coagulate the material proximate to the nasal sinus.

3. The apparatus according to claim 2, wherein the low frequency AC potential has a power of up to 5 W and a frequency of up to 30 KHz.

4. The apparatus according to claim 1, further comprising a generator, wherein the generator is configured to generate the electrical potential as a high frequency AC (alternating current) potential, and wherein the generator is connected to the conductive leads so as to apply the high frequency AC potential between the first electrode and the second electrode to ablate the material proximate to the nasal sinus.

5. The apparatus according to claim 4, wherein the high frequency AC potential has a power of up to 20 W and a frequency greater than 30 kHz.

6. The apparatus according to claim 1, further comprising an insulating section separating the distal end into a distal section comprising the distal tip, and a proximal section comprising the location proximal to the distal tip.

7. The apparatus according to claim 1, wherein the guidewire is configured as a coil.

8. An apparatus, comprising:
   (a) a guidewire, having a distal end and a proximal conductive section proximal to the distal end and insulated therefrom, the distal end and the proximal conductive section being dimensioned to penetrate into a nasal sinus;
   (b) a balloon, which is slidably fitted directly over the guidewire in proximity to the distal end such that the balloon is in contact with the guidewire;
   (c) an inflation channel, which runs along the guidewire and is coupled to convey a pressurized fluid into the balloon so as to inflate the balloon;
   (d) an electrode, fixedly attached to a distal tip of the guidewire, wherein the electrode and the proximal conductive section are distal and separate from the balloon; and
   (e) conductive leads running along the guidewire and coupled to apply an electrical potential between the electrode and the proximal conductive section of the guidewire so as to treat material proximate to the nasal sinus.

9. The apparatus according to claim 8, further comprising a generator, wherein the generator is configured to generate the electrical potential as a low frequency AC (alternating current) potential, and wherein the generator is connected to the conductive leads so as to apply the low frequency AC potential between the electrode and the proximal conductive section to coagulate the material proximate to the nasal sinus.

10. The apparatus according to claim 9, wherein the low frequency AC potential has a power of up to 5 W and a frequency of up to 30 KHz.

11. The apparatus according to claim 8, further comprising a generator, wherein the generator is configured to generate the electrical potential as a high frequency AC (alternating current) potential, and wherein the generator is connected to the conductive leads so as to apply the high frequency AC potential between the electrode and the proximal conductive section to ablate the material proximate to the nasal sinus.

12. The apparatus according to claim 11, wherein the high frequency AC potential has a power of up to 20 W and a frequency greater than 30 kHz.

13. The apparatus according to claim 8, wherein the guidewire is configured as a coil.

14. An apparatus comprising:
   (a) a coil having a distal end dimensioned to penetrate into a nasal sinus;
   (b) a balloon slidably fitted directly over the coil in proximity to the distal end such that the balloon is in contact with the coil;
   (c) an inflation channel running along the coil and configured to convey a pressurized fluid into the balloon so as to inflate the balloon;
   (d) a first conductive element fixedly attached to a distal tip of the coil;
   (e) a second conductive element at a location proximal to the distal tip, wherein the first and second conductive elements are distal and separate from the balloon; and
   (f) conductive leads running along the coil and configured to apply an electrical potential between the first and second conductive elements so as to treat material proximate to the nasal sinus.

15. The apparatus according to claim 14, wherein the first conductive element includes a first electrode, wherein the second conductive element includes a second electrode fixedly attached to the coil.

16. The apparatus according to claim 14, wherein the first conductive element includes an electrode, wherein the second conductive element includes a proximal conductive section of the coil proximal to the distal end and insulated therefrom, the proximal conductive section being dimensioned to penetrate into the nasal sinus.

17. The apparatus according to claim 14, further comprising a generator, wherein the generator is configured to generate the electrical potential as a low frequency AC (alternating current) potential, and wherein the generator is connected to the conductive leads so as to apply the low frequency AC potential between the first conductive element and the second conductive element to coagulate the material proximate to the nasal sinus.

18. The apparatus according to claim 17, wherein the low frequency AC potential has a power of up to 5 W and a frequency of up to 30 KHz.

19. The apparatus according to claim 14, further comprising a generator, wherein the generator is configured to generate the electrical potential as a high frequency AC (alternating current) potential, and wherein the generator is connected to the conductive leads so as to apply the high frequency AC potential between the first conductive element and the second conductive element to ablate the material proximate to the nasal sinus.

20. The apparatus according to claim 19, wherein the high frequency AC potential has a power of up to 20 W and a frequency greater than 30 kHz.

* * * * *